United States Patent [19]

Berg

[11] Patent Number: Plant 6,843

[45] Date of Patent: Jun. 13, 1989

[54] ROSE PLANT NAMED WINTONBURY PARISH

[75] Inventor: David H. Berg, Bloomfield, Conn.

[73] Assignee: The First Congregational Church of Bloomfield, Bloomfield, Conn.

[21] Appl. No.: 153,668

[22] Filed: Feb. 8, 1988

[51] Int. Cl.[4] ..... A01H 5/00

[52] U.S. Cl. ..... Plt./7

[58] Field of Search ..... Plt. 7

*Primary Examiner*—Robert E. Bagwill

*Attorney, Agent, or Firm*—Nancy J. Linck

[57] ABSTRACT

A new miniature rose variety having uniquely colored semi-double flowers wherein the bottom two-thirds of the petal is white and the top one-third is light red.

1 Drawing Sheet

The present invention relates to a new and distinct variety of rose plant of the miniature rose class which was originated by my crossing as seed parent "Poker Chip" (U.S. Plant Pat. No. 4,582) with the pollen of the variety known as "Lady X" (U.S. Plant Pat. No. 2,691). The varietal denomination of this new variety is "Berpar".

This new variety has novel characteristics which distinguish it from its parents and all other varieties of which I am aware. Among the novel characteristics it possesses are its unusual semi-double blooms which are white at the base and center of the petals with the top one-third of the petal colored light red of exhibition form and which are long-lasting in the fully open stage. Asexual reproduction by budding of the new variety as performed in Bloomfield, CT, shows that the foregoing and other distinctive characteristics come true to form and are established and transmitted through succeeding propagations.

The accompanying illustration shows typical specimens of the vegetative growth and flowers of my new variety in different stages of development, depicted in color as nearly true as it is reasonably possible to make the same in a color illustration of this character.

The following is a detailed description of my new variety. The color terminology is in accordance with The Royal Horticultural Society Colour Chart. The terminology used in my color description refers to plate numbers in The Royal Horticultural Society Colour Chart, e.g., "4B" refers to plate 4B.

Parentage of seedling:

*Seed parent.*—"Poker Chip".

*Pollen parent.*—"Lady X".

Class: Miniature.

FLOWER

Observations were made from specimens grown outside at Bloomfield, Conn., in August, 1987.

Blooming habit: Near continuous.

Bud:

*Size.*—Medium to large.

*Form.*—Long pointed.

*Color.*—When sepals first divide - White 155 A with occasional petals and tips of petals red-purple 57A; When petals unfurl predominant color is White 155A with flushes of red-purple 57A.

*Sepals.*—Slightly longer than bud.

*Peduncle.*—About ¼" in length; aspect: straight; strength: erect; color, green 141D.

Bloom:

*Size.*—When fully expanded, 2⅜ to 2½ inches.

*Borne.*—Singly with very occasional spray.

*Form.*—High centered through ⅓ open stage then becoming flat; petals reflex upon opening.

*Petalage.*—Number under normal conditions: 14–18.

*Color.*—After sepals fall, color remains stable as described above under "Bud" description until ⅓ open; as the bloom becomes fully open the outer side of the petal is 155A for the lower half and shading upward to the top of the petal from 62C to 58D to 57C; inside of the petal is 155A for the lower half and shades upward to 62D.

*Fragrance.*—Very slight.

Petals:

*Texture.*—Thick.

*Appearance.*—Matte inside; smooth and satin-like outside.

*Form.*—Pointed and reflexed.

*Arrangement.*—Symmetrically arranged.

*Petaloids.*—Few, if any.

*Persistance.*—Does not drop until flower is completely dead.

*Lastingness.*—Relatively short in the ¼ to ⅓ open stage; very longlasting in the fully open stage.

REPRODUCTIVE ORGANS

Stamens, filaments, and anthers:

*Arrangement.*—Regularly arranged around styles.

*Color.*—Filament, 4B; Anther, 15C.

Styles: Even, medium length.

Stigmas:

*Color.*—33C.

PLANT

Form: Upright and spreading.

Growth: Vigorous, with long stems.

*Height attained.*—15 to 20 inches.

Folage:

*Size.*—Medium.

*Quantity.*—Abundant.

*Number of leaflets.*—5 to 7.

*Color.*—New foliage — upper side 183A; under side, 181A; Old foliage — upper side 137B; under side, 147C.

*Shape.*—Elongated/pointed.

*Texture.*—Upper side is glossy; under side is matte.

*Edge.*—Serated.

*Seration.*—Serrulate.

*Stipules.*—Medium.

*Disease resistance.*—Blackspot, good; mildew, average; rust, good.

Wood:

*New wood.*—Color, 45C; bark smooth.

*Old wood.*—Color, 143A; bark smooth.

Thorns: Very few and widely spaced.

Prickles: Few, if any.

Winter hardiness: Requires ordinary protection in extreme climates.

I claim:

1. A new and distinct variety of rose plant of the miniature rose class, substantially as shown and described, characterized particularly by its uniquely colored semi-double flowers wherein the bottom two-thirds of the petal is white and the top one-third is light red and wherein the petals are symmetrically arranged, pointed, and reflexed.

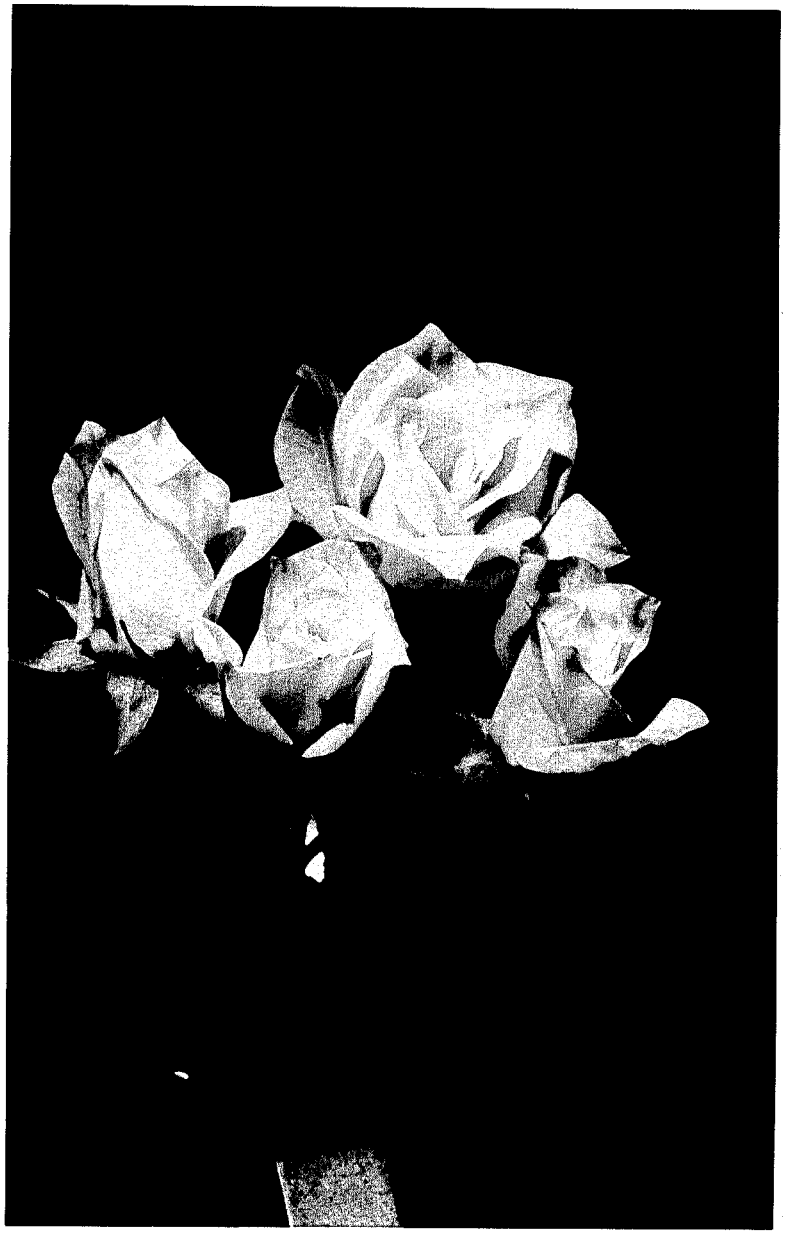

* * * * *